(12) United States Patent
Misra

(10) Patent No.: US 10,052,293 B2
(45) Date of Patent: Aug. 21, 2018

(54) CURCUMIN INFUSED MILK BEVERAGE AND A PROCESS FOR THE PREPARATION THEREOF

(71) Applicant: Srikumar Misra, Odisha (IN)

(72) Inventor: Srikumar Misra, Odisha (IN)

( * ) Notice: Subject to any disclaimer, the term of this patent is extended or adjusted under 35 U.S.C. 154(b) by 78 days.

(21) Appl. No.: 15/252,919

(22) Filed: Aug. 31, 2016

(65) Prior Publication Data

US 2018/0055787 A1 Mar. 1, 2018

(51) Int. Cl.
*A61K 31/12* (2006.01)
*A23L 2/58* (2006.01)
*A23L 2/56* (2006.01)
*A23C 9/156* (2006.01)

(52) U.S. Cl.
CPC .............. *A61K 31/12* (2013.01); *A23C 9/156* (2013.01); *A23L 2/56* (2013.01); *A23L 2/58* (2013.01); *A23V 2002/00* (2013.01)

(58) Field of Classification Search
CPC .... A61K 31/12; A61K 47/183; A61K 9/0019; A61K 9/0095; A61K 31/5415; A61K 45/06; A61K 47/10; A61K 47/26; A23L 2/58; A23L 2/56; A23C 9/156; A23V 2002/00
USPC ........................................................ 514/679
See application file for complete search history.

(56) References Cited

U.S. PATENT DOCUMENTS

2013/0129680 A1* 5/2013 Lines .................. A61K 31/375
424/85.7

FOREIGN PATENT DOCUMENTS

IN 1785MU2013 A * 7/2015 ............... A23L 2/38

OTHER PUBLICATIONS

Bharat B. Aggarwal, Chitra Sundaram, Nikita Malani and Haruyo Ichikawa, Curcumin: The Indian Solid Gold, Advances in Experimental Medicine and Biology • Feb. 2007.

Subash C. Gupta, Sridevi Patchva and Bharat B. Aggarwal, Therapeutic Roles of Curcumin: Lessons Learned from Clinical Trials, The AAPS Journai, vol. 15, No. 1, Jan. 2013.
Robert A DiSilvestro, Elizabeth Joseph, Shi Zhao and Joshua Bomser, Diverse effects of a low dose supplement of lipidated Curcumin in healthy middle aged people, Nutr J. 2012;11(1):79.
Chattopadhyay, Ishita; Biswas, Kaushik; Bandyopadhyay, Uday; Banerjee, Ranajit K (2004) Turmeric and Curcumin: biological actions and medicinal applications, Current science, Jul. 10, 2004, 87 (1). pp. 44-53. ISSN 0011-3891.
Wilken R, Veena MS, Wang MB, Srivatsan ES.Curcumin: A review of anti-cancer properties and therapeutic activity in head and neck squamous cell carcinoma. Molecular Cancer. 2011;10:12. doi:10. 1186/1476-4598-10-12.
Radha K. Maheshwari, Anoop K. Singh, Jaya Gaddipati, Rikhab C. Srimal, Multiple biological activities of Curcurnin: A short review, Life Sciences, vol. 78, Issue 18, Mar. 27, 2006, pp. 2081-2087, ISSN 0024-3205, http://dx.doi.org/10.1016/j.lfs.2005.12.007.
N.P. Aditya, SheetalAditya, Han-Joo Yang, Hye Won Kim, Sung Ook Park, Jinhee Lee, SanghoonKo, Curcumin and catechin co-loaded water-in-oil-in-water emulsion and its beverage application, Journal of Functional Foods, vol. 15, May 2015, pp. 35-43, ISSN 1756-4646.
LiqiangZou, BingjingZheng, Wei Liu, Chengmei Liu, Hang Xiao, David Julian McClements, Enhancing nutraceutical bioavailability using excipient emulsions: Influence of lipid droplet size on solubility and bioaccessibility of powdered Curcumin, Journal of Functional Foods, vol. 15, May 2015, pp. 72-83, ISSN 1756-4646.
S. RahimiYazdi, M. Corredig, Heating of milk alters the binding of Curcumin to casein micelles. A fluorescence spectroscopy study, Food Chemistry, vol. 132, Issue 3, Jun. 1, 2012, pp. 1143-1149.
GRAS Report on Curcumin for FDA Approval. 2013. Available at http://www.fda.gov/downloads/food/ingredientspackaginglabeling/gras/noticeinventory/ucm346902.pdf last visited on May 10, 2015.

* cited by examiner

*Primary Examiner* — Rachael E Bredefeld
*Assistant Examiner* — Ibrahim D Bori
(74) *Attorney, Agent, or Firm* — Rothwell, Figg, Ernst & Manbeck, P.C.

(57) ABSTRACT

A Curcumin infused milk beverage composition comprising 0.05% to 0.15% alkalized Curcumin, standardized milk with fat, sugar and stabilizing agents, wherein the pH of resultant composition is maintained at 6.8.

9 Claims, No Drawings

CURCUMIN INFUSED MILK BEVERAGE AND A PROCESS FOR THE PREPARATION THEREOF

CROSS-REFERENCE TO RELATED APPLICATIONS AND PRIORITY

The present application does not claim priority from any other patent application(s).

TECHNICAL FIELD

The present disclosure in general relates to a food beverage, and more particularly to the curcumin infused milk beverage and a process for the preparation thereof.

BACKGROUND

The invention relates to a ready to drink functional health milk beverage and process for commercial production of the same. More particularly, it relates to a ready to drink functional health milk beverage which is infused with Curcumin, having excellent product stability, long shelf life and a good taste resulting in neither aggregation nor precipitation of Curcumin, and a process for commercial production of the same.

The plant *Curcuma longa* L. commonly known as turmeric is a spice of the botanical family Zingiberaceae originated in India. Turmeric has many medicinal uses identified in Ayurveda, Unani and traditional Chinese medicine systems for hundreds of years. The rhizome of the plant Turmeric is derived. Turmeric has a bitter taste and is yellowish in colour. The active molecule called Curcumin or diferuloylmethane is a yellow pigment present in turmeric. Additionally, the powdered extracts of turmeric-dried roots may contain volatile and non-volatile oils, proteins, fat, minerals, carbohydrates and moisture.

According to the review article by Aggarwal B B, Sundaram C, Malani N, Ichikawa H. Curcumin: The Indian solid gold. Adv Exp Med Biol. 2007; 595: 1-75, "Curcumin has been shown to exhibit antioxidant, anti-inflammatory, antiviral, antibacterial, antifungal, and anticancer activities and thus has a potential against various malignant diseases, diabetes, allergies, arthritis, Alzheimer's disease, and other chronic illnesses. These effects are mediated through the regulation of various transcription factors, growth factors, inflammatory cytokines, protein kinases, and other enzymes".

Curcumin binds to a variety of proteins and inhibits the activity of various kinases. According to a review article by Aggarwal B B, Sung B. Pharmacological basis for the role of curcumin in chronic diseases: an age-old spice with modern targets. Trends. Pharmacol Sci. 2009 February; 30(2):85-94, "Extensive research within the past two decades has shown that Curcumin mediates its anti-inflammatory effects through the down regulation of inflammatory transcription factors (such as nuclear factor kappaB), enzymes (such as cyclooxygenase 2 and 5 lipoxygenase) and cytokines (such as tumor necrosis factor, interleukin 1 and interleukin 6)."

In human clinical trials, Curcumin has been found to be safe and efficacious, and as per Generally Recognized as Safe (GRAS) notification 460, the U.S. Food and Drug Administration has approved Curcumin as a "generally regarded as safe" compound.

A review article on clinical human trials of Curcumin, Gupta S C, Patchva S, Aggarwal B B. Therapeuticroles of curcumin: lessons learned from clinical trials. AAPS J. 2013 January; 15(1):195-218, summarizes that "some promising effects have been observed in patients with various pro-inflammatory diseases including cancer, cardiovascular disease, arthritis, uveitis, ulcerative proctitis, Crohn's disease, ulcerative colitis, irritable bowel disease, tropical pancreatitis, peptic ulcer, gastric ulcer, idiopathic orbital inflammatory pseudo tumor, oral lichen planus, gastric inflammation, vitiligo, psoriasis, acute coronary syndrome, atherosclerosis, diabetes, diabetic nephropathy, diabetic microangiopathy, lupus nephritis, renal conditions, acquired immunodeficiency syndrome, β-thalassemia, biliary dyskinesia, Dejerine-Sottas disease, cholecystitis, and chronic bacterial prostatitis."

According to a study published in a paper by Disilvestro R A, Joseph E, Zhao S, Joshua B. Diverse effects of a low dose supplement of lapidated curcumin in healthy middle aged people. Nutr J. 2012; 11 (1):79, the participants were given either lapidated curcumin (80 mg/day) or placebo for 4 weeks. Curcumin, but not placebo, produced decrease in salivary amylase and in the plasma levels of triglycerides, beta amyloid, alanine amino transferase, and sICAM.

The turmeric paste and powder contains Curcumin (diferuloylmethane) at a very low percentage, 3% to 4% according to "Chattopadhyay, Ishita; Biswas, Kaushik; Bandyopadhyay, Uday; Banerjee, Ranajit K (2004) Turmeric and curcumin: biological actions and medicinal applications Current science, 87 (1). pp. 44-53. ISSN 0011-3891."

A review article on clinical human trials of Curcumin, Gupta S C, Patchva S, Aggarwal B B. Therapeuticroles of curcumin: lessons learned from clinical trials. AAPS J. 2013 January; 15(1):195-218, summarizes all the ongoing clinical trials on Curcumin. It can be observed that concentration of Curcumin consumed can be found to be at a range of 0.2 to 8 gm per day.

It is marketed in several forms, including capsules, tablets, ointments, energy drinks, soaps, and cosmetics. Use of turmeric infused milk in India is well known but the milk gives a bitter taste and cannot be stored for longer time as it results in sedimentation and coagulation of milk proteins.

Use of purified Curcumin in food products is not as easy as that of turmeric. Curcumin is not water soluble and is generally extracted from turmeric by organic solvents based extraction followed by crystallization. Curcumin is stable at high temperatures and in acids, but unstable in alkaline conditions and in the presence of light. The photo-stability of Curcumin under light when in a dissolved state is very low. When a transparent container is filled up with the beverage in which Curcumin is dissolved, Curcumin content gets deteriorated with the lapse of time by the irradiation light.

Japanese patent JP5094466B provides a solution to Curcumin in a composition which is hard to dissolve in water and causes precipitation of Curcumin containing particles when preserved for a long period of time. This composition is prepared by crushing Curcumin containing particles to 210-420 nm in the presence of an emulsifier and an aqueous solvent. This makes it more water dispersible, retaining high stability to light, causing no precipitation when stored for long period of time and having no bad influence on palate feeling and flavor of food and drink added therewith. This patent provides a method of mixing Curcumin crystals (95% of purity) with decaglycerine stearic acid ester, decaglycerinpulmitic acid ester, enzymatically decomposed lecithin, heating and dissolving in 85 degrees C., then cooled to 30 degrees Celsius, and further adding 25 kg of glycerine, 0.1 kg of potassium carbonate, and 0.05 kg of sodium chloride.

Finally, pulverizing the mixture in a bead mill and bringing the particle size to 210-420 nm. It also describes use of Curcumin composition so obtained to be used in food and drinks including cow milk but at a very low concentration thus may have limited bioavailability to be effective as a functional beverage. Again, this process involves complex process of using Curcumin with a particle size of 210-420 nm which may not be commercially viable. Furthermore, the chemicals used in this process, decaglycerin stearic acid ester, decaglycerinpulmitic acid, glycerin, potassium carbonate, sodium chloride may not be appropriate for a functional health beverage.

Additionally, JP2009028042A provides Curcumin containing turmeric drink which is excellent to disperse in water, has precipitation stability and also provides a process for making the same. This invention uses turmeric as raw material and provides a process for preparation of a "curcmaerhizome" and this curcmaerhizome is used as the basic component of a curcmaerhizoma beverage. The invention sets the Curcumin of quantity to 30 to 60 mg on the basis of 100 ml of beverages and is stabilized by stirring 0.01 to 0.05% by weight of gellant gum at 2000 to 5000 rpm for 5 to 15 minutes to 80 to 95 degrees C. hot water. This is a water based beverage and it does not teach the use milk.

[Additionally, WO2004081023A1 provides a method of preparation of a water-soluble Curcumin by covalent bonding sugar to the Curcumin, thereby making the Curcumin, which was insoluble to water, into a water-soluble Curcumin. This water soluble Curcumin may be applied to more fields such as food, soluble drugs and dyes.

Accordingly, there is a long felt need for a milk based Curcumin beverage that can be prepared in an efficient and simple manner without compromising the efficacy of Curcumin. Additionally, there is a need for a stable Curcumin milk beverage with good dispersibility, low precipitation, high photo-stability, long shelf life, and good taste as well, and suitable for industrial production.

SUMMARY OF THE INVENTION

In one aspect the invention is a Curcumin infused milk beverage comprising 0.05% to 0.15% alkalized Curcumin, standardized milk with fat, sugar and stabilizing agents wherein the pH of resultant composition is maintained at 6.8.

In another aspect, the invention relates to a process of preparing a Curcumin infused milk beverages comprising the steps of:
a) adding standardized milk at a temperature of 6 to 8 degree Celsius into a product mixing tank.
b) adding an alkalized Curcumin solution, and a mixture of sugar and Carrageenan into a product mixing tank, wherein the quantity of sugar and Carrageenan are in the ratio of 10:1.
c) mixing for 5 minutes with continuous agitation.
d) transferring the final batch of the product to a Ready Beverage tank.
e) adding flavours and colours to the Ready Beverage tank and mixing with continuous agitation.
f) processing the mixture at 140 degrees Celsius for 4 seconds with 250/50 bar upstream homogenization.

In yet another aspect, the invention relates to a manufacturing process for preparing a Curcumin infused milk beverages comprising the steps of:
a) taking a batch of 9000 kg milk at 4 to 8 degree Celsius into a product mixing tank and standardize milk to have a specific fat content.
b) preparing an alkalized Curcumin solution and a dry mixture of ten parts sugar and one-part Carrageenan.
c) recirculation of the standardized milk through a blender
d) selecting PHE in Chilling profile and giving set point of 6 to 15 degree Celsius.
e) adding a dry mixture of sugar and Carrageenan through a blender.
f) mixing the batch for 5 to 10 minutes with continuous agitation.
g) adding remaining sugar through Blender as per batch card.
h) adding an alkalized Curcumin solution through a blender.
i) transferring the final batch of the product to the Ready Beverage tank.
j) adding colour and flavouring agents and mixing properly for 20 minutes.
k) processing at 140 degrees Celsius for 4 seconds with 250/50 bar upstream homogenization.
l) packaging the beverage through aseptic packaging.

DETAILED DESCRIPTION

The following description is full and informative description of the best method and composition presently contemplated for making the present invention which is known to the inventors at the time of filing the patent application. Of course, many modifications and adaptations will be apparent to those skilled in the relevant arts in view of the following description in view the appended claims. While the product and process described herein are provided with a certain degree of specificity, the present technique may be implemented with either greater or lesser specificity, depending on the needs of the user. Further, some of the features of the present technique may be used to advantage without the corresponding use of other features described in the following paragraphs. As such, the present description should be considered as merely illustrative of the principles of the present technique and not in limitation thereof, since the present technique is defined solely by the claims.

As a preliminary matter, the definition of the term "or" for the purpose of the following discussion and the appended claims may be intended to be an inclusive "or". That may be, the term "or" may be not intended to differentiate between two mutually exclusive alternatives. Rather, the term "or" when employed as a conjunction between two elements may be defined as including one element by itself, the other element itself, and combinations and permutations of the elements. For example, a discussion or recitation employing the terminology "A" or "B" includes: "A" by itself, "B" by itself and any combination thereof, such as "AB" and "BA." It may be worth noting that the present discussion relates to exemplary embodiments, and the appended claims should not be limited to the embodiments discussed herein.

As will be appreciated by people skilled in the art, to best understand the present invention, it is a Curcumin infused milk beverage and a manufacturing process of preparation of the same using a simple but efficient method that results in a stable beverage composition overcoming the technical problem of low solubility and stability of Curcumin in a solution.

The prior art as described in above paragraphs clearly points that Curcumin is unstable in an alkaline solution and loses its golden yellow colour above a pH of 7.5. When pure Curcumin (95%) is dissolved in water, it gives a pH of 6.1. Even at a concentration of 30% solution of Curcumin, prepared by 30 gms of Curcumin in 70 gm hot water, kept in water bath at 55 degrees Celsius for 10 minutes and cooled to 25 degrees Celsius, it has an acidic pH. This Acidic pH of Curcumin is not suitable for making flavoured milk products. Any ingredient having pH less than 6.4 adversely affect milk proteins. The present invention solves this problem by optimizing the exact pH of Curcumin infused milk beverage so that the properties of beverage are preserved and good dispersibility and stability of Curcumin is obtained in the final composition.

The pH is kept below 7.0 but above 6.4, thus making the resultant solution slightly acidic but not affecting the milk proteins. Curcumin is easily soluble in alkali solution, although here the resultant solution is slightly acidic, Curcumin gets dissolved by addition of milk and sugar. To achieve dispersibility and avoid precipitation of Curcumin, milk with fat content is used along with sugar. It is found that standardized milk with low concentration of fat gives the desired results. In the manufacturing process, standardized milk at a temperature of 6 to 8 degree Celsius is used along with sugar. A stabilizing agent is used to maintain the dispersibility of Curcumin in the milk.

Standardized milk refers to milk in which adjustment have been made with respect to raising or lowering of fat and SNF (solids not fat) levels of milk. The Standardized Milk in the invention refers to milk having the preferred concentration of up to 3.4% Fat and 9.53% SNF.

Preparation of this milk beverage involves use of 95% pure Curcumin which is water insoluble. The particle size of the Curcumin is about 125 micrometers and 95% of Curcumin can pass through 125 micrometers sieve and rest 5% is larger than 125 micrometers. In the final product, the Curcumin concentration is kept at a low concentration of 0.05% (wt/wt percentage for a batch). The concentration of Curcumin can go up to 0.15%. (wt/wt percentage for a batch) for particular milk beverage products. Thus, in an exemplary situation a 160 ml package of this milk beverage has approximately 80 mg of Curcumin and which can go up to 240 mg as required for ingestion.

In the prior art there are no such beverage which has been able to pack this much amount of Curcumin without compromising on precipitation and stability. And no such beverage was identified which is milk based beverage infused with Curcumin.

The stability of prepared Curcumin infused milk beverage was studied with different shelf life periods. The pH was used as the parameter to find the stability of packaged product. The table 1 provided the pH of samples over period of time. The products with different chocolate & fruit flavours were tested separately. The study points to a remarkable stability of the product over a period of six months.

TABLE 1

Shelf Life of Curcumin infused milk beverages

| Shelf Life in Days | Mango | Chocolate | Strawberry Peach | Badam |
|---|---|---|---|---|
| 0 | 6.7 | 6.7 | 6.7 | 6.69 |
| 120 | | | 6.69 | 6.63 |
| 180 | 6.62 | 6.73 | | |

The products may be packaged in Tetra Pak packaging which also enhances stability of the end product by preventing photo-reaction of the Curcumin beverage. The Tetra Pak packaging material has four layers of protection with one layer of paperboard, two layer of polythene and one layer of aluminium. The Curcumin milk beverage is packaged in the Tetra Pak packages and has stability against light.

EXAMPLE 1: Manufacturing Process

In one exemplary mode of carrying out the Invention, in a single batch, 9000-kilogram of milk is used at a temperature of 4 to 8 degree Celsius. This milk may be added into a product mixing tank. The milk is pre-treated and skimmed to have standardized amount of Fat and SNF content. The preferred concentration of 3.4% Fat and 9.53% SNF is used for preparation of this milk beverage.

For a 9000 kg batch the ingredients and their amounts are specified in the table given below:

TABLE 2

Ingredients and Flavoring agents with preferred amounts

| Ingredients | Range | Quantity Range in 9000 Kg Batch (in kgs) | |
|---|---|---|---|
| Curcumin | 0.05%-0.15% | 4.5 | 13.5 |
| Cocoa Powder | 1.6%-2.4% | 144 | 216 |
| Sugar | 8% | 720 | |
| Carrageenan 1 | 0.02%-0.04% | 1.8 | 3.6 |
| Carrageenan 2 | 0.014%-0.018% | 1.06 | 1.62 |
| Carrageenan 3 | 0.019%-0.021% | 1.71 | 1.89 |
| Beta-carotene | 0.00375%-0.0055% | 1.01 | 1.49 |
| Flavouring agents | | | |
| Vanilla Flavour | 0.1%-.15% | 9 | 13.5 |
| Caramel Colour DS | 0.055%-0.075% | 4.95 | 6.75 |
| Kesar Badam Flavour | 0.24%-0.26% | 21.6 | 23.4 |
| Strawberry Flavour | 0.15%-0.2% | 13.5 | 18 |
| Peach Flavour | 0.020%-0.030% | 1.8 | 2.7 |
| Mango Flavour | 0.18%-0.20% | 16.2 | 18 |

All these ingredients are used for preparing Curcumin infused milk beverage but the flavouring agents are used for preparing milk beverages of different flavours. The table given below summaries the used flavours:

TABLE 3

Flavouring Agents and their Use

| Ingredients | Use |
|---|---|
| Cocoa Powder | Only in Chocolate |
| Vanilla Flavour | Only in Chocolate |
| Caramel Colour DS | Only in Chocolate |
| Kesar Badam Flavour | Only in Badam |
| Strawberry Flavour | Only in Peachy-Strawberry |
| Peach Flavour | Only in Peachy-Strawberry |
| Mango Flavour | Only in Mango |

All the ingredients are prepared separately which are then added in the product mixing tank in a single batch preparation. In one embodiment the ingredients are prepared by the following processes:

EXAMPLE 2: Process of Making Alkalized Curcumin Solution 1. 1% hot water (wt/wt percentage with respect to the batch size in kilograms) at 55 degrees Celsius in the formulation is used for Curcumin solution preparation. Here, 90 kg of water is used to which 4.5 kg of Curcumin (95% purity) is added.

2. 0.5% (wt/wt percentage with respect to the batch size in kilograms) water is used for preparation of 50% Disodium Phosphate (DSP) solution. To 45 kg of water, 45 kg of Disodium Phosphate is added to prepare 50% Disodium Phosphate (DSP) solution.
3. The Curcumin solution needs to be alkalized by adding the 50% Disodium Phosphate (DSP) solution to it.
4. The pH of the mixture is calibrated to a pH of 6.8 by continuously adding DSP solution.

EXAMPLE 3: Mixture of Sugar and Carrageenan

1. A dry mixture of sugar and Carrageenan are prepared by taking ten-part sugar and one-part Carrageenan or in a ratio of 10:1. Both Carrageenan 1 and Carrageenan 2 are used for this mixture preparation. Different Carreagenans have different functionalities like product stabilisation and Mouth feel (texture). Since the use of different type of stabilisers is not permitted under the FDA regulations, different grades of Carrageenan are used.
2. The content of Carrageenan is kept at 0.34 to 0.58% of the batch and amount of sugar kept at 3.4% to 5.8%. In a batch of 9000 kg, 52.2 kg sugar, 3.6 kg Carrageenan 1 and 1.62 kg Carrageenan 2 are added.
3. Sugar and Carrageenan are mixed through a blender, preferably through a ventury mixture.

EXAMPLE 4: Cocoa Slurry is Prepared by the Following Process 1. 7.5% (wt/wt percentage with respect to the batch size in kilograms) water is to be heated to 55 degree Celsius and cocoa powder is to be mixed in it. In a 9000 kg batch, 675 kg of water is used to which 162 kg of cocoa powder is added.
2. The temperature is to be increased to 90 to 92 degree Celsius and maintained for 45 minutes with slow agitation.
3. After 45 minutes, slurry is to be cooled to 45 to 50 degree Celsius.

The example given here is for preparation of Curcumin infused milk beverage with a chocolate flavour. In addition to other ingredients, preparation of milk flavoured Curcumin milk beverage uses cocoa slurry, vanilla flavour, Caramel Colour DS and an additional stabilizing agent Carrageenan 3. The quantities of all these ingredients to be added are as specified in table 2.

The milk in the product mixing tank is initiated into recirculation through a ventury mixer, preferably through a blender. Then the PHE is selected in Chilling profile and given a set point of 6 to 15 degree Celsius.

The dry mixture of sugar and Carrageenan prepared in the previously described process is added to the product mixing tank through a blender. Any other blender can be used in place of a ventury mixing. As described in product ingredient table, sugar amount is kept at 8% of the total batch; part of the sugar is used for preparing this dry mixture of sugar and Carrageenan. The other part of sugar is added to the product mixing tank. The ingredients in the product mixing tank are mixed for 5 to 10 minutes with continuous agitation.

For chocolate flavoured Curcumin milk beverage, another dry mixture of sugar and Carrageenan 3 are prepared by using ten parts sugar and one-part Carrageenan 3. Amount of Carrageenan 3 is kept at 0.019% to 0.021% wt/wt of total batch and the amount of sugar kept at 0.19% to 0.21% of the total batch. This is added through a blender such as ventury mixing.

The alkalized Curcumin solution prepared by a process described above is added through a blender. The amount of Curcumin is kept at 0.05% to 0.15% wt/wt of the batch.

The cocoa slurry prepared as per the process described above is added to the product mixing tank and mixed for 4 to 7 minutes with continuous agitation. The cocoa amount is kept at 1.6% to 2.4% wt/wt percentage of the batch.

After proper mixing, the batch in the product mixing tank is transferred to a Ready Beverage tank for final processing and packaging.

As per the table 3, the Curcumin infused milk beverage is prepared with a number of different flavours. Beta-carotene is used as a colouring agent for all the products. But for chocolate flavour Curcumin milk beverage, Caramel Colour DS is additionally used. Caramel Colour DS is added to the Ready Beverage tank at an amount as per the table 2. For chocolate flavour, vanilla flavour is added at an amount as specified in table 2 to the ready Beverage tank. The batch is mixed properly for 20 minutes.

The batch is processed at 140° C. for 4 seconds with 250/50 bar upstream homogenization and followed by packaging the product in Tetra Pak™ containers through aseptic packaging process. Here the package contains in an exemplary embodiment about 160 ml of curcumin infused milk beverage.

The upstream homogenization is a high pressure treatment of milk preferably at 250/50 bar of pressure to avoid creaming and provide better mouth feeling of milk. In absence of such homogenization it is observed that the fat membranes leak 'free fat' during sterilization resulting in 'fat plug' (butter) in to the pack. Homogenization gives a full fat flavour even at lower fat content and make the milk look whiter.

As will be appreciated by a person skilled in the art, the various implementations of the present technique provide a variety of advantages. For example, Curcumin infused milk beverage can be further fortified with other vitamins and minerals.

The foregoing description is presented to enable a person of ordinary skill in the art to make and use the invention and is provided in the context of the requirement for obtaining a patent. The present description is the best presently contemplated method for carrying out the present invention. Various modifications to the preferred embodiment will be readily apparent to those skilled in the art and the generic principles of the present invention may be applied to other embodiments, and some features of the present invention may be used without the corresponding use of other features. Accordingly, the present invention is not intended to be limited to the embodiment shown but is to be accorded the widest cope consistent with the principles and features described herein.

Many modifications of the present invention will be apparent to those skilled in the arts to which the present invention applies. Further, it may be desirable to use some of the features of the present invention without the corresponding use of other features.

Accordingly, the foregoing description of the present invention should be considered as merely illustrative of the principles of the present invention and not in limitation thereof.

What is claimed is:

1. A Curcumin infused milk beverage composition comprising 0.05% to 0.15% alkalized Curcumin, standardized milk with fat, sugar and stabilizing agents characterized in that the pH of resultant composition is maintained to be greater than 6.4 but less than 7.

2. The milk beverage composition as claimed in claim 1 wherein said milk beverage also comprises a flavoring agent and one or more coloring agents.

3. The milk beverage as claimed in claim 1 wherein said alkalized Curcumin is prepared by adding a 50% Disodium Phosphate solution to a 5% to 15% solution of 95% pure Curcumin with particle size of 125 micrometers in hot water at 55 degrees Celsius and calibrating the resulting solution to the pH 6.8.

4. The milk beverage as claimed in claim 1 wherein said standardized milk is maintained at a temperature of 6 to 8 degree Celsius.

5. The milk beverage as claimed in claim 1, wherein said stabilizing agents is a mixture of natural linear polysaccharide comprising at least Carrageenan.

6. The milk beverage as claimed in claim 2, wherein said flavoring agent is selected from a group consisting of cocoa powder, vanilla flavor, strawberry flavor, peach flavor, mango flavor, caramel flavour and Kesar Badam flavour.

7. The milk beverage as claimed in claim 5 wherein said natural linear polysaccharide content is kept at 0.34% to 0.58% wt/wt of the beverage.

8. The milk beverage as claimed in claim 1 wherein said coloring agents are selected from the group consisting of Beta-carotene and natural coloring pigments.

9. The milk beverage as claimed in claim 1, wherein said Standardized Milk has a concentration of up to 3.4% Fat and 9.53% solids-not-fat (SNF).

\* \* \* \* \*